(12) United States Patent
Jaunakais et al.

(10) Patent No.: US 7,333,194 B2
(45) Date of Patent: Feb. 19, 2008

(54) PHOTOMETRIC ANALYSIS

(75) Inventors: Ivars Jaunakais, Rock Hill, SC (US);
Sanjay Mohan Anand, Charlotte, NC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 309 days.

(21) Appl. No.: 11/157,944

(22) Filed: Jun. 22, 2005

(65) Prior Publication Data
US 2006/0066858 A1 Mar. 30, 2006

Related U.S. Application Data

(63) Continuation-in-part of application No. 11/117,536, filed on Apr. 29, 2005, and a continuation-in-part of application No. 10/949,315, filed on Sep. 27, 2004.

(51) Int. Cl.
*G01N 21/01* (2006.01)
(52) U.S. Cl. .................................... 356/246
(58) Field of Classification Search ............... None
See application file for complete search history.

(56) References Cited

U.S. PATENT DOCUMENTS

| | | | |
|---|---|---|---|
| 3,833,864 A | 9/1974 | Kiess et al. | |
| 3,937,613 A | 2/1976 | Rosicky | |
| 4,275,031 A | 6/1981 | Fischer et al. | |
| 4,353,869 A | 10/1982 | Guth | |
| 5,298,978 A | 3/1994 | Curtis et al. | |
| 5,534,441 A | * 7/1996 | Miyazaki et al. | 436/517 |

OTHER PUBLICATIONS

Hach, *DR/890 Colorimeter Procedures Manual*, Orientation of Sample Cells, p. 25 (1997).
Hach, *Water Analysis Handbook*, 4th Ed., Orientation of Sample Cells, Matching of Sample Cells, pp. 36-37 (2002).
Palintest, Operation Instructions sheet (undated prior art).
Lamotte Company, *1200 Colorimeter Manual*, pp. 10-11, and Chlorine Test Procedure Sheet (undated prior art).
Myron L Company, *TechPro Operation Manual Model ARH1*, pp. 1-3, 6-9, and 14-16 (2002).
Myron L Company, *Ultrameter Operation Manual Model 6P*, pp. 1-3, 7-11, and 24-26 (2002).
Oakton Instruments, *Instruction Manual C401/301/201/102/101 Portable Colorimeter*, pp. 1, 3,6-8, and 36 (2004).

* cited by examiner

*Primary Examiner*—Tu T Nguyen
(74) *Attorney, Agent, or Firm*—Timothy R. Kroboth

(57) ABSTRACT

A beneficial photometric analytical method is described according to which an effective amount of at least one analytical agent for photometric analysis, is delivered from a support into a liquid sample, and advantageously a mixing action may be provided, by moving a portion of the support in the sample. The sample may be added to a photometric cell disposed in a photometric instrument, or may be added to a photometric instrument cell chamber (or well). In accordance with an advantageous feature of the method, the photometric instrument is beneficially waterproof. A photometric cell that provides more than one optical path length may beneficially be used, and a particular optical path length selected by rotation of the photometric cell in the cell chamber. Also described is a beneficial photometric apparatus.

23 Claims, 6 Drawing Sheets

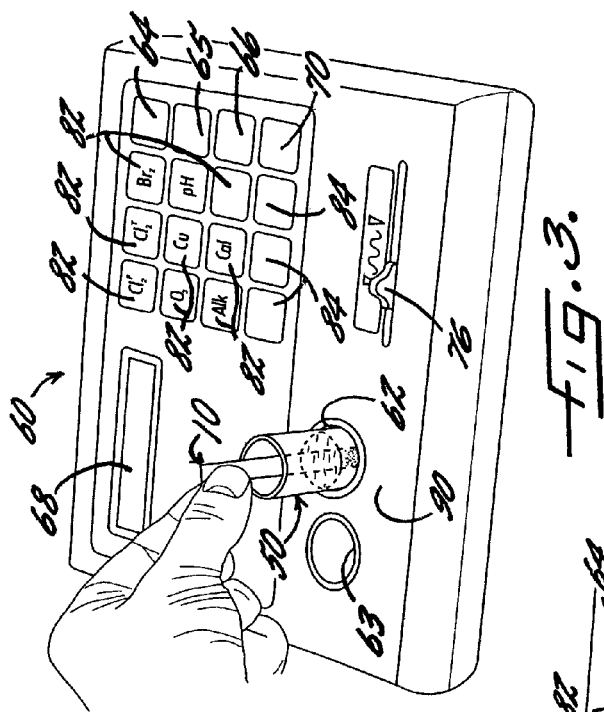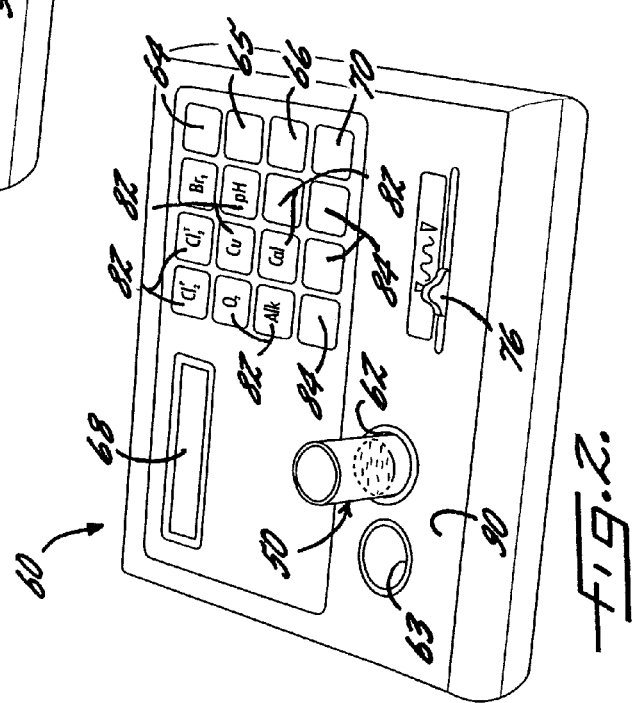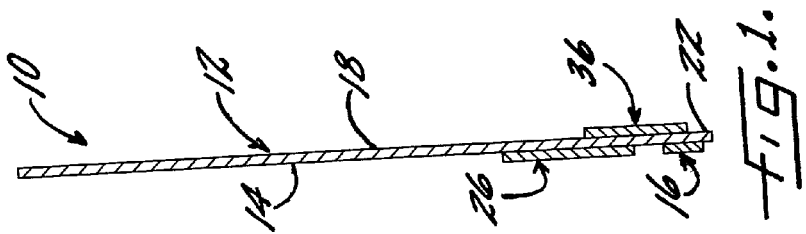

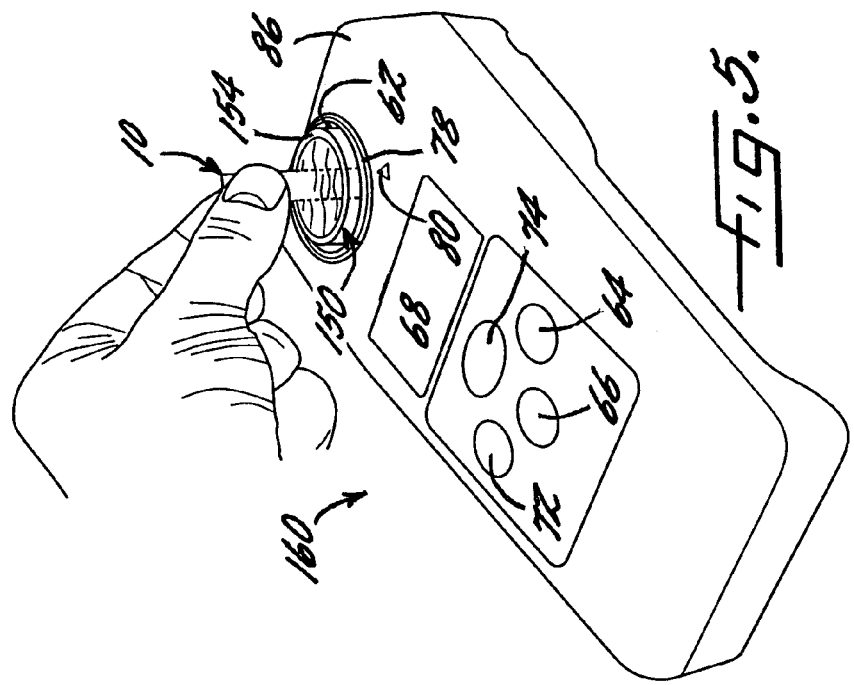

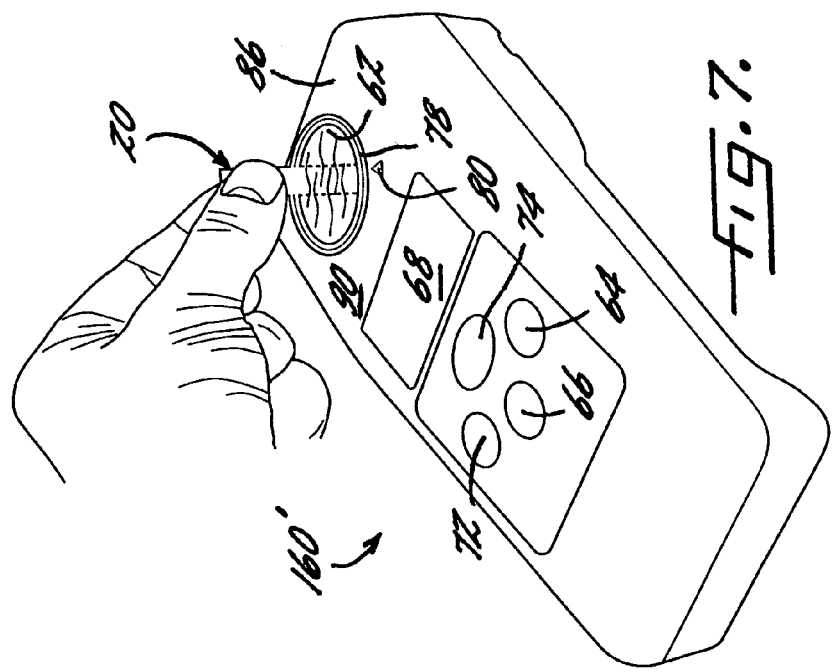

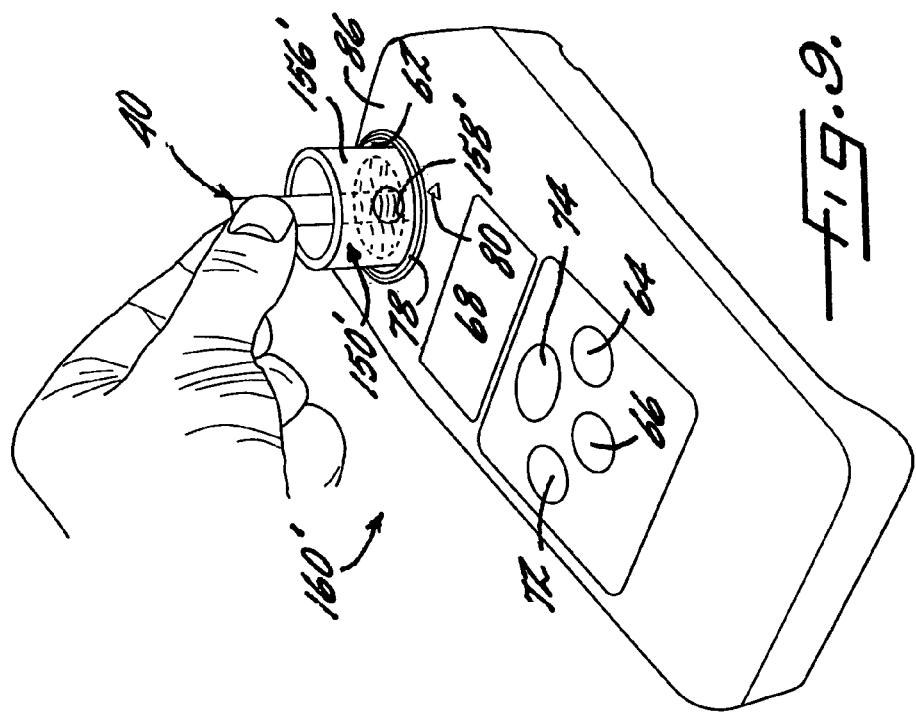
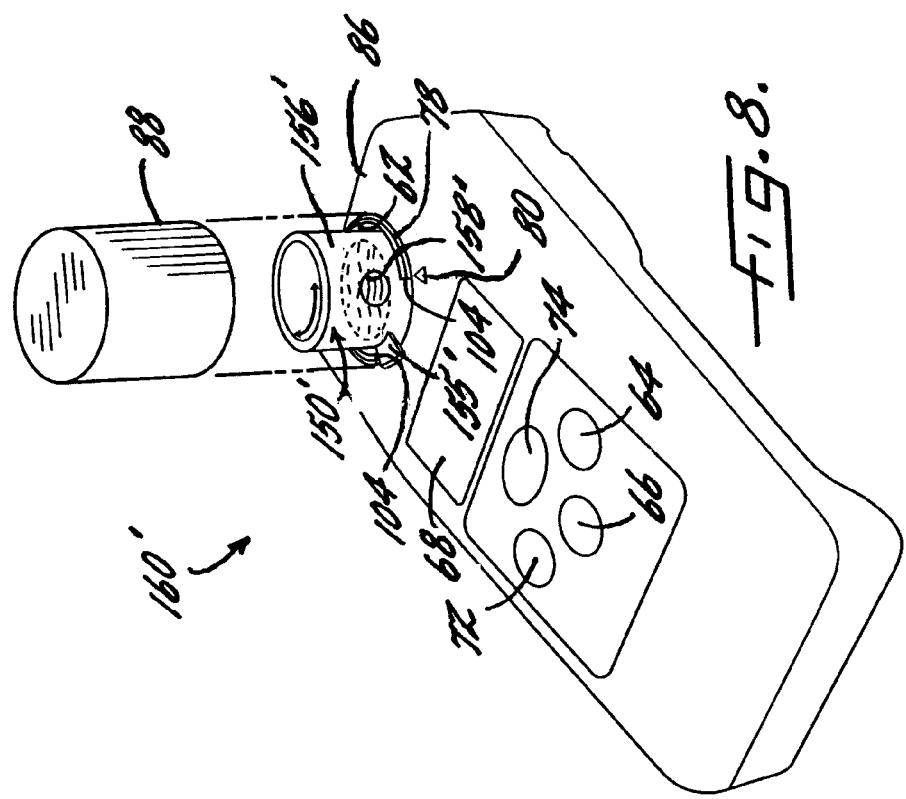

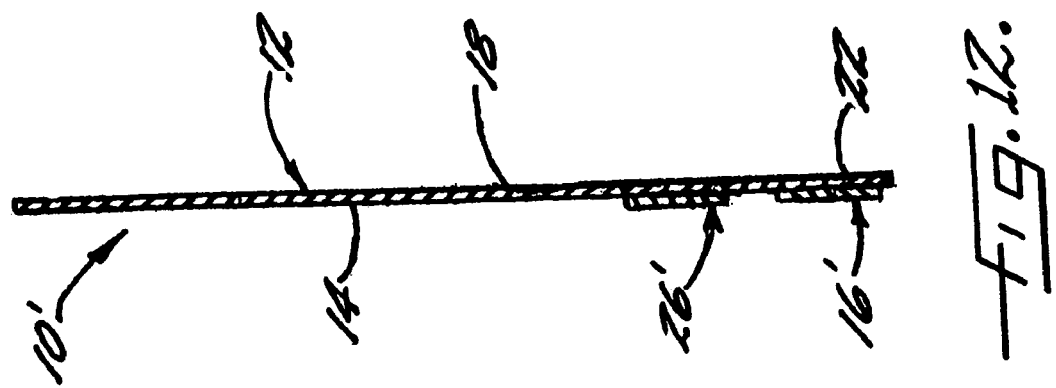
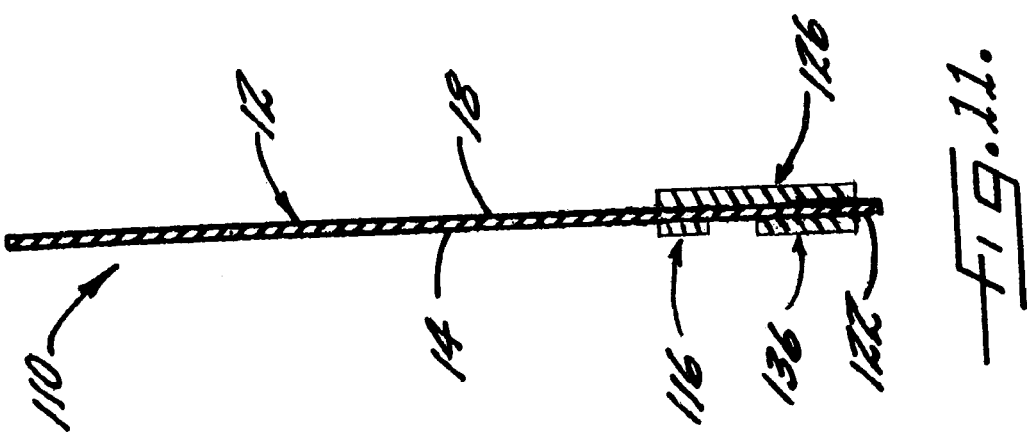
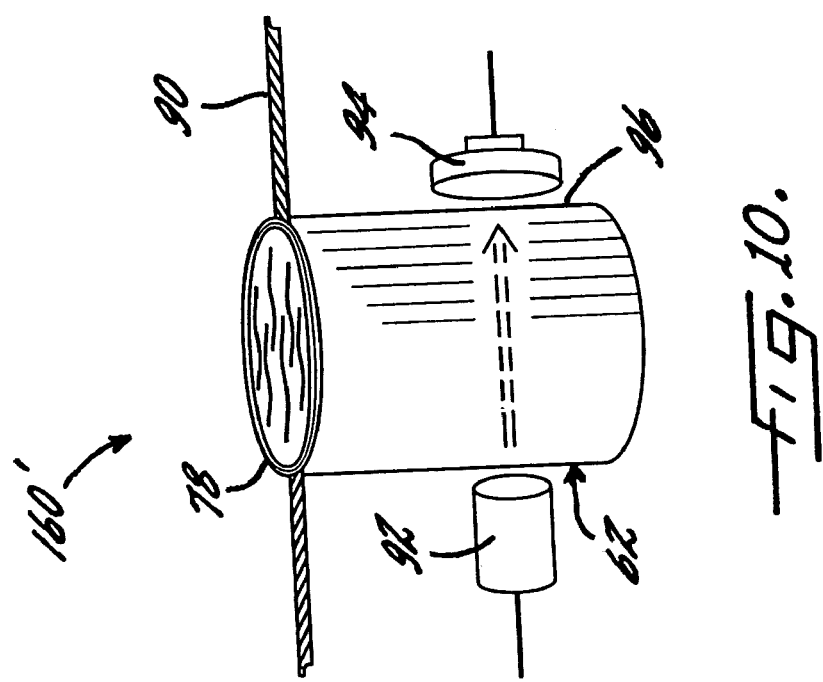

PHOTOMETRIC ANALYSIS

REFERENCE TO EARLIER FILED PATENT APPLICATIONS

This patent application is a continuation-in-part of pending U.S. patent application Ser. No. 10/949,315, filed on Sep. 27, 2004, and of pending U.S. patent application Ser. No. 11/117,536, filed on Apr. 29, 2005.

FIELD OF THE INVENTION

This invention relates to photometric analysis of liquids.

BACKGROUND OF THE INVENTION

Photometric analysis of liquids typically uses two photometric cells (or cuvettes) or one photometric cuvette. When two matched cuvettes are used, a first cuvette with sample is used as a blank to zero the photometric instrument, and then an optical value for an analyte of interest is obtained using a matched cuvette with sample to which analytical agents have been added. It is recognized that nicks and scratches from handling may cause an optical mismatch between cuvettes and introduce error into the test results. Accordingly, it is customary to discard matched cuvettes that have been nicked or scratched.

When one cuvette is used, the cuvette with sample is inserted into the photometric instrument as a blank to zero the instrument, and after zeroing the instrument and removing the cuvette, analytical agents are added to the sample, and then the cuvette is re-inserted into the instrument to obtain an optical value for an analyte of interest. It is recognized that because cuvette orientation in a photometric instrument will greatly affect test results, a cuvette should always be inserted into the instrument so that the cuvette has the same orientation to the light path, and that variability in the geometry and quality of the glassware can cause variability in results.

Furthermore, it is recognized regardless whether one or two cuvettes are used, that a cuvette exterior should be free of smudges or fingerprints or water droplets to ensure accurate readings. Useful photometric instruments include filter photometers, photometers without filters, and spectrophotometers, and typically provide an optical path length of 1 cm or longer. Photometric analysis of liquids includes colorimetric analysis and turbidimetric analysis. By "turbidimetric analysis" is meant, for purposes of this description, analysis based upon measuring the effect of fine suspended particles on a light beam.

As illustrated by U.S. Pat. No. 4,353,869 to Guth, it has been described to photometrically test for intoxication by inserting an end of a bubbler tube into an analytical agent-containing liquid contained in a glass ampoule, by then inserting the resulting assembly into a photooptical apparatus, by then nulling the photooptical apparatus, and by then bubbling deep lung breath from a suspect through the end of the bubbler tube into the liquid and taking a photometric reading. A mixing action is provided by the deep lung air bubbling through the analytical agent-containing liquid.

A pH/conductivity, water resistant meter that includes a conductivity cell with built-in electrodes and a pH sensor well, is commercially available from Myron L Company of Carlsbad, Calif. The pH sensor includes a protective cap. The meter is not useful for photometric analysis.

Also described in the prior art, as illustrated by U.S. Pat. No. 3,937,613 to Rosicky and U.S. Pat. No. 4,275,031 to Fischer et al, are reagent delivery devices that include a support such as an inert plastic strip or the like, and that release certain analytical agents into a sample for calorimetric evaluation of sample color. The sufficiently rigid supports of such devices may be used to stir the sample. Fisher et al teach the use of certain embedding polymers that dissolve in water to release analytical agents and form an optically clear solution, and disclose a broad range of embedding polymers, analytical agents, and analyses.

As can be recognized from the foregoing description of photometric analysis prior art, there continues to be a need for improved photometric analysis of liquids. It would be beneficial to minimize manipulations, reduce the time and labor required for analysis, and to reduce variability of measurements. It would be beneficial is to avoid the need for matched cuvettes, and to avoid any concern about the use of cuvettes with nicks or scratches.

SUMMARY OF THE INVENTION

In accordance with a first aspect of a beneficial inventive photometric analysis method, a photometric cell (or cuvette) containing an aqueous sample, is inserted into a suitable photometric instrument. Alternatively in accordance with a second aspect of a beneficial inventive photometric analysis method, an aqueous sample is added to a photometric cell disposed in a suitable photometric instrument. In accordance with a modification of the second aspect, the aqueous sample is added to the cell chamber (or well) of a suitable photometric instrument normally used for receiving a photometric cell for optical analysis.

Thereafter, in accordance with the beneficial photometric analysis method, an effective amount of at least one water soluble analytical agent for optical analysis, is delivered from a support of a reagent delivery device into the aqueous sample, and advantageously a mixing action may be provided, by moving a portion of the support in the aqueous sample. To this end, the support may beneficially be of sufficient rigidity for providing effective mixing. Then, the support is withdrawn from the resulting liquid, and thereafter the liquid in the photometric cell or photometric instrument well is photometrically analyzed.

Depending upon the analysis, the analyte of interest may be reacted, prior to the analytical agent delivery step, to yield a useful reaction product, and the reaction product may thereafter be reacted to produce a photometrically analyzable liquid. In other analyses, an analytical agent delivered from a reagent delivery device, reacts with the analyte of interest to produce a photometrically analyzable liquid. In yet other analyses, an analytical agent reactive with the analyte of interest to produce a photometrically analyzable liquid, is added prior to the analytical agent delivery step.

It will be recognized by one skilled in the art upon consideration of the detailed description of the inventive photometric technology, that yet other analyses within the scope of the inventive photometric technology, involve variations from those just described, and furthermore that although a reagent delivery device typically delivers a reactive analytical agent, an analytical agent delivered from a reagent delivery device, may merely assist or otherwise promote a desired optical analysis. Moreover, depending upon the analysis of interest or as appropriate or desired, more than one reagent delivery device may be used to deliver a useful analytical agent or agents prior to the photometric analysis step.

Beneficially, in accordance with the invention when a photometric cell is used, a blank reading is obtained for the aqueous sample and photometric cell prior to analytical agent addition, and the photometric cell remains in the instrument until after a desired analysis or analyses. Prior to the blank reading, in the case of a particularly useful photometric cell that provides for selection between different optical path lengths, a desired optical path length may beneficially be selected by photometric cell rotation. After a desired analysis or analyses, the photometric cell may then be withdrawn from the photometric instrument. Advantageously, in accordance with the modification when the photometric instrument well is used instead of a photometric cell, a blank reading is likewise obtained prior to analytical agent addition.

In accordance with the second inventive aspect, the sample is beneficially added to the photometric cell or photometric instrument well, by immersing a portion of the photometric cell or photometric instrument well in a bulk volume of an aqueous liquid to be analyzed, such as swimming pool or spa water, and thereafter withdrawing the photometric cell or photometric instrument well from the aqueous liquid. Advantageously, in accordance with the second inventive aspect, the photometric instrument is a waterproof photometric instrument. By the term "waterproof" is meant, for purposes of this description, impervious to water, and is to be distinguished from water-resistant. The imperviousness of a waterproof photometric instrument beneficially protects function-critical instrument components, including but not limited to, electronic and power components, from contact with water. The photometric instrument well of a particularly beneficial waterproof photometric instrument, is located near an end of the photometric instrument.

When a photometric cell is immersed for sample collection, a peripheral wall of the photometric cell may beneficially be provided with a sample-volume controlling aperture, or the photometric cell may be beneficially dimensioned including having a height selected to capture a desired sample volume. The sample-volume controlling aperture is advantageously sized to allow escape of excess collected sample from the photometric cell through the aperture. Excess liquid is allowed to escape through the aperture to capture a desired sample volume in the photometric cell.

In accordance with a further inventive aspect, a particularly useful photometric cell that provides more than one optical path length is disposed in a photometric instrument, and an optical path length is selected by rotation of the photometric cell. Thereafter, an effective amount of at least one analytical agent for photometric analysis, is added to a liquid sample in the photometric cell, and thereafter the liquid in the photometric cell is photometrically analyzed. This further inventive aspect is not limited to use with a reagent delivery device. In accordance with this further inventive aspect, the photometric cell advantageously remains in the photometric instrument until after a photometric analysis. Beneficially, if desired or appropriate for the analysis of interest, for instance when an over-range result is found, a shorter optical path length for estimation, may be selected by rotation of the photometric cell. Thereafter, the same analytical agent may be added to a fresh liquid sample using the newly selected optical path length, and photometric analysis effected.

Also provided is a beneficial photometric apparatus that includes a photometric instrument provided with a cell chamber for receiving a photometric cell for analysis, wherein the cell chamber is partially surrounded by a raised rim. The apparatus advantageously further includes a photometric cell that provides more than one optical path length, and comprises a flange. The photometric cell is rotatably disposed in the photometric instrument cell chamber, and the rotation of the photometric cell is limited by contact of the flange with an end of the raised rim, and an optical path length of the photometric cell is thereby positioned relative to a light path of the photometric instrument. This beneficial photometric apparatus is not limited to use with a reagent delivery device.

Advantageously, useful cuvettes or a useful photometric instrument well may be discolored, nicked or scratched in the optically important region. Prior to this invention, discolored, nicked or scratched cuvettes have normally been discarded.

In the drawing and in detailed description of the invention that follows, there are essentially shown and described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIG. 1 is a longitudinal cross-sectional view of a reagent delivery device useful in the present invention;

FIG. 2 is a perspective view of a useful photometric instrument, with a photometric cell inserted in the cell chamber;

FIG. 3 is a perspective view of the photometric instrument of FIG. 2, with the delivery end of the reagent delivery device of FIG. 1 in the photometric cell;

FIG. 4 is a perspective view of a useful waterproof photometric instrument, with a photometric cell inserted in the cell chamber, showing the photometric cell immersed to collect a sample for analysis;

FIG. 5 is a more detailed perspective view of the photometric instrument of FIG. 4, illustrating that a desired sample volume is captured by the immersion, and showing the delivery end of the reagent delivery device of FIG. 1 in the photometric cell;

FIG. 6 is a perspective view of another useful waterproof photometric instrument but without a photometric cell in the cell chamber (or well), showing the well immersed to collect a sample for analysis;

FIG. 7 is a more detailed perspective view of the photometric instrument of FIG. 6, illustrating that a desired sample volume is captured by the immersion, and showing the delivery end of a reagent delivery device for optical analysis, in the photometric instrument well;

FIG. 8 is a perspective view of a modification of the waterproof instrument of FIGS. 6 and 7, showing a modified photometric cell inserted in the cell chamber and exposed to view by exploded positioning of an interfering light-blocking cap, and illustrating the rotatable photometric cell in a first position relative to the photometric instrument light path, and that the modified instrument and photometric cell provide controlled photometric cell positioning for selection of a desired photometric cell optical path length;

FIG. 9 is a perspective view of the photometric instrument of FIGS. 6 and 7 without the light-blocking cap and other beneficial features shown in FIG. 8, illustrating that a desired sample volume is captured by a volume-controlling aperture of the photometric cell depicted, and the delivery end of a reagent delivery device for optical analysis, in the photometric cell;

FIG. 10 is a partial cross-sectional simplified, schematic illustration of a portion of the photometric instrument of FIGS. 6 and 7, showing the photometric instrument well containing a collected sample, and a light path from a light source, through the well, and to a light detector;

FIGS. 11 to 13 are longitudinal cross-sectional views of three additional reagent delivery devices useful in the present invention;

DETAILED DESCRIPTION OF THE INVENTION

Figure 15:
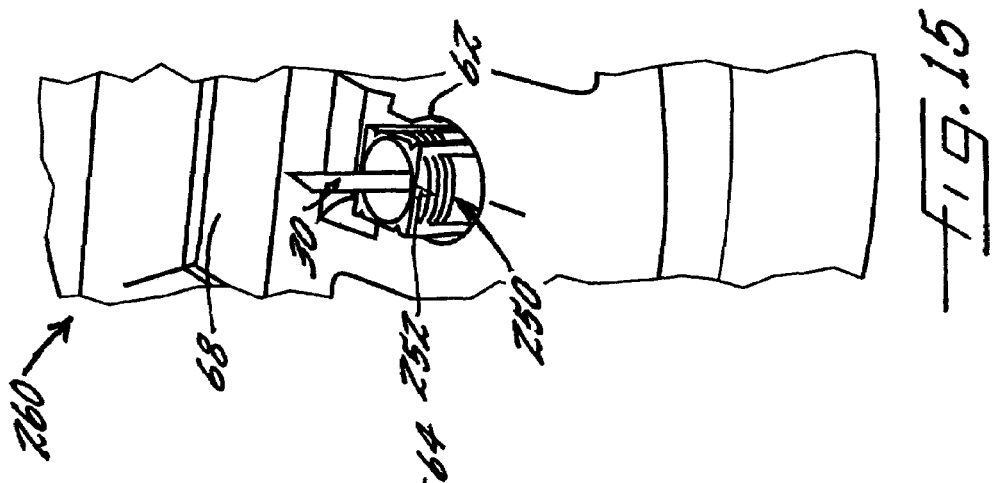
FIG. 15 is a partial, enlarged view of the photometric instrument of FIG. 14, with the delivery end of the reagent delivery device of FIG. 13 in the microcuvette.

The inventive photometric technology is useful for a wide range of analyses, with a limiting feature typically being the use of a reagent delivery device for analytical agent delivery. As a result, the inventive photometric technology may be touch-free. Accordingly, user handling of reagent solutions or tablets or powders or glass ampoules may be eliminated. In such case, there are no tablets to crush or dissolve, powders to spill, and glass ampoules to break, there is no potential for injury from broken glass ampoules, and any concern about the effect of any reagent spillage or loss, on precision is removed.

However, it is not a necessary feature of the inventive photometric technology, in its broadest aspect, that any or all analytical agents be delivered using a reagent delivery device. To the contrary, if appropriate or desired, analytical agents may be added prior to, or after, analytical agent delivery using a reagent delivery device. A further consideration relative to applications of the inventive technology, is that when an impregnated fibrous matrix is used as the analytical agent carrier, useful analytical agents are beneficially solids, not liquids.

Beneficially, manipulations can be minimized, the time and labor required for analysis can be reduced, and variability of measurements can be reduced. Advantageously, concerns about cuvette orientation in a photometric instrument, or about the use of nicked, scratched or discolored cuvettes are overcome.

The inventive photometric technology has wide commercial applicability, and is useful for testing drinking water, pool and spa water, aquarium water, pond water, industrial and environmental water, and for other types of water testing. Medical applicability includes biochemical and diagnostic testing based upon analysis of an aqueous liquid, including for example, urine testing, and furthermore includes testing of equipment such as dialysis equipment to confirm removal of chlorine and chloramine contaminants. Further applications include food processing, and analysis of plant material.

Referring to FIGS. 1 and 11-13 of the drawing, illustrative analytical agent delivery devices are shown. As illustrated, an analytical agent delivery device useful in the present invention, conveniently includes an elongated support or handle member 12, which may beneficially be a plastic strip or other suitable support of sufficient rigidity for providing stiffness for an effective mixing action. As a result, the support may be used not only as a carrier for analytical agents, but also a mixing action may be provided by moving a portion of the support in the sample.

Typically, when a plastic strip is used, the support will range in thickness from about 0.006 to 0.020 inches. However, the support thickness may, if appropriate or desired, vary from this range depending upon the particular goal or goals for its application. When a sample volume of about 2 ml or less is analyzed, and accordingly use of a microcuvette is advantageous, a practical width for support 12 will typically range from about 4 to 10 mm. The width of the support may be 12 mm or more when a larger sample volume is analyzed, or may vary from this range, if desired or appropriate, depending upon the particular goal or goals for its application.

Any other suitable support, such as a rod, in particular of square or rectangular cross-section, may be used if desired or appropriate. Although an elongated shape of the support is advantageous for delivery and mixing, it will be recognized that other shapes may be used for the support. The support may be made from various inert materials, with preferred materials for economy being available at low cost. Suitably, the support may be made of, for example, PVC.

An analytical agent delivery device useful in the present invention, beneficially provides for touch-free delivery of appropriate water soluble analytical agents for the analysis of interest into the liquid being analyzed. Conveniently, to this end, and referring again for sake of illustration to FIGS. 1 and 11 to 13, disposed on a first face 14 of the support, or on the first face and an opposite support face 18, are one or more carriers 16,26,36,116,126,136,16',26',36' for one or more analytical agents. It will be readily recognized that variations in the location and number of carriers on a support from those described and illustrated, can be used. Thus, variations include fewer or more carriers; for instance, Example 1 includes a description of a useful reagent delivery device having one carrier. A carrier or carriers may, for example, provide increased analytical agent loading, provide for physical separation of analytical agents, whether incompatible or not, or provide an additional analytical agent or agents.

Conveniently, the carriers of a useful reagent delivery device may be water absorbent fibrous pads that maintain structural integrity during analysis, and that are impregnated with analytical agents. A suitable fibrous pad should be non-linting, or minimally linting, that is, should release few, if any, fibers into the sample.

Materials useful as suitable fibrous pads are known, and include filtration materials that include cellulosic and synthetic fibers. Depending upon the analysis of interest, useful filtration materials when the carriers are fibrous matrices, are illustrated by, but not limited to, Schleicher and Schuell (S&S) 404 and 497 papers, which are cellulosic papers having a thickness of about 0.2 mm, S&S 593 paper, which is a cellulosic paper having a thickness of about 0.35 mm and a water absorbency value of about 2.8 g/100 $cm^2$ as determined by ASTM 3285 or TAPPI T441 (difference in weight of a 10×10 sheet weighed dry, and re-weighed after immersion for 10 seconds in deionized water), S&S 8S paper, which is a rayon paper having a thickness of about 0.35 mm and a water absorbency value of about 2.4 g/100 $cm^2$, and Lohmann Vliesstoffe OL 50 paper, a viscose rayon paper having a thickness of about 0.4 mm.

Depending upon the analysis and analytical agent, a plurality of pads, whether impregnated or not, may form a stacked structure in which case the structure thickness may be up to 3 mm or more. Useful carriers are not limited to fibrous pads, and include, but are not limited to, water-insoluble polymers.

Furthermore, depending upon the analysis and analytical agent, instead of a fibrous matrix, a carrier for an analytical agent may be a suitable water soluble material that by dissolution in water, delivers the analytical agent, and that forms an optically clear solution. Suitable water soluble carriers for use in the inventive photometric technology include, but are not limited to, those described in the Fisher et al patent, which describes certain solid or waxy organic polymers as embedding polymers, deposition thereof on a support, and useful relative ratios. For sake of brevity, the disclosure thereof at col. 3, line 31, to col. 4, line 2, and at col. 5, line 65, to col. 6, line 13, is hereby incorporated herein by reference.

However, if free chlorine analysis within one minute of introducing a water soluble carrier for a DPD salt into a sample, is desired, a mildly acidic carboxylic acid such as 2,2-bis(hydroxymethyl)propionic acid, would be selected as the carrier. Thus, it is essential that the water soluble carrier selected not interfere with test accuracy or objectives. Otherwise, the inventive technology, in its broadest aspect, is not constrained by the carrier selected, or in what way or how an analytical agent is carried on a useful reagent delivery device.

When an analytical agent is deposited on a support with a suitable water soluble material as the carrier, the relative ratio (weight) of analytical agent to carrier will depend upon considerations that include the desired analytical agent loading, and can be expected to vary widely. Beneficially, to obtain an excess loading, for instance, of DPD salt, the amount of the DPD salt may exceed that of the carrier, and in particular may substantially exceed the amount of the carrier. For example, a ratio (weight) of DPD salt to carrier in the range of about 4:1 to 10:1 and greater may be used. An appropriate lower limit for the relative ratio (weight) of an analytical agent to carrier may be 0.01:1 or lower.

Moreover, depending upon the analytical agent, if desired or appropriate, the carrier may be entirely omitted, as illustrated in a variation described in Example 1. To this end, a solution of the analytical agent in a suitable solvent or solvent system may be deposited on the support, and a drying step follows.

As previously described, the inventive photometric technology is useful for a wide range of analyses, with a limiting feature typically being the use of a reagent delivery device for analytical agent delivery. Thus, appropriate water soluble analytical agents for use in the present invention vary widely, although when an impregnated fibrous matrix is used as the carrier, useful analytical agents are beneficially solids, not liquids. Furthermore, useful analytical agents include, but are not limited to, agents reactive with analytes of interest, agents reactive with reaction intermediates resulting from reaction with analytes of interest, stabilizing or stabilization-assisting agents, buffer agents, water soluble barrier-forming agents, dispersing agents, wetting agents, and any other reagents that assist or otherwise promote the desired optical analysis. Specific analytical agents include, but are not limited to, those described in the Examples that follow, and those described at col. 4, line 25, to col. 5, line 42, of the Fisher et al patent, which disclosure for sake of brevity, is hereby incorporated herein by reference, except for certain of those analytical agents such as dithizone, that are not water soluble. Furthermore, to be useful, an analytical agent cannot interfere with test accuracy or objectives.

Specifically disclosed by Fisher et al, at col. 5, lines 10-11, is inorganic phosphate analysis using a molybdate/reducing agent combination. Phosphate analysis is useful for testing drinking water, pool and spa water, industrial waters including boiler and cooling tower waters, waste water, and for other types of water testing. Many U.S.A. cities add about 1 ppm phosphate to drinking water to reduce pipe corrosion. Phosphates are a limiting nutrient for algae growth in a pool or pond. As indicated by Fisher et al, the chemistry of reacting molybdate ions with phosphate ions to yield a phosphate molybdate complex, and reducing the phosphate molybdate complex to yield a reduced complex for calorimetric analysis, is known in the prior art.

As can be thus understood, carriers of useful analytical agent delivery devices are beneficially impregnated with, or otherwise carry, a plurality of appropriate water soluble analytical agents for the analysis of interest. A suitable carrier loading of a particular analytical agent will vary depending upon considerations including the particular analytical agent selected, the extent of delivery of the analytical agent, the analyte concentration, and the volume to be analyzed. Thus, for example, a relatively higher analyte concentration or a relatively greater volume can generally be expected to require a relatively higher carrier loading, whereas a relatively lower carrier loading may be appropriate for a relatively lower analyte concentration or relatively smaller volume. As can be readily recognized, the loading of particular analytical agents will vary greatly depending upon the analysis of interest, objectives of the analysis including the desired speed of analysis, and the foregoing considerations typically in particular the analyte concentration and volume. Thus, although carrier loading of a particular analytical agent may generally range from about 0.00005 to 0.2 g for a typical 10 ml sample, a higher or lower carrier loading may be appropriate or desired. In any event, useful reagent delivery devices carry, and deliver into the liquid being analyzed, effective amounts of appropriate analytical agents for the analysis of interest.

When an impregnated fibrous pad carrier is used, the pad may incorporate a water soluble barrier. A benefit is that it tends to seal an analytical agent within the fibrous pad. As a result, abrasive loss of the analytical agent from the pad may be minimized, and the barrier tends to isolate the analytical agent from any user or oxygen contact.

A mildly acidic, water soluble analytical agent may be used to form the water soluble barrier. By "mildly acidic" is meant for purposes of this description, that the barrier-forming agent has a pH in water in the range of about 3 to 5.5. Especially illustrative is a carboxylic acid having a pH in water in the range of about 3 to 4, such as 2,2-bis(hydroxymethyl)propionic acid. This type of agent is not polymeric.

A useful amount of the barrier-forming agent will vary depending upon the particular agent selected. The water soluble barrier-forming agent may be added to an impregnation solution in an amount ranging from about 0.5 to 10 wt. % or more, conveniently from about 1 to 5 wt. %.

Fibrous pad impregnation may be accomplished in any of several ways. A suitable way is to pass a carrier material through an impregnation bath containing the particular chemicals so that the carrier becomes saturated with the impregnation solution. The carrier may be then dried at room temperature or at an elevated temperature. Advantageously, the concentration of the chemicals in an impregnation solution and the residence time of the carrier material in the solution are selected to ensure impregnation of an appropriate loading. Generally speaking, residence time will vary from about two to forty seconds, depending upon the loading desired and the carrier. If desired or appropriate, the carrier may be dipped more than once to increase the loading.

Depending upon the analysis of interest, prior to or in preparation for analysis, a sample may be prepared by conventional procedures that make the analyte of interest available for analysis. Sample pH and any other significant sample parameter should be known or determined, and if not acceptable, the sample should be appropriately adjusted.

The sample size may vary from 1 ml or less, to 50 ml or more, depending upon the analysis of interest and the analysis objectives. For example, according to US EPA accepted standard methodology for free chlorine analysis, a water sample size of 10 ml is used.

Useful photometric instruments typically provide a 1 cm or longer light path, and include, but are not limited to, filter photometers, photometers without filters, and spectrophotometers. Useful filter photometers include Palintest Pooltest 9 photometers, available from Palintest Ltd, Tyne & Wear, England, and CO7500 Colorimeter photometers available from Industrial Test Systems, Inc., Rock Hill, S.C. Useful photometers without filters include Oakton Colorimeter C201 and C401 photometers, available from Oakton Instruments, Vernon, Ill., Palintest 1000 Chlorometer-Duo photometers, and Hach Pocket Colorimeter II photometers, available from Hach Company, Loveland, Colo.

Waterproof photometric instruments are especially useful when a sample is collected by immersing a portion of the photometric cell or photometric instrument well in an aqueous liquid to be analyzed. Useful waterproof photometric instruments include the Oakton Colorimeter C201 and C401 photometers.

With reference to FIG. 10, a simplified schematic view of a portion of a useful waterproof photometric instrument 160' shows an upper housing wall 90 provided with a cell chamber or well 62 for receiving a photometric cell, a suitable light source 92, and a suitable light detector 94. Well 62 includes a peripheral wall 96 advantageously provided with an optical window for a light path through the well. Conveniently, the well is disposed between the light source and light detector, as is the case for tranmissive photometry, and the optical window provides a light path from the light source, through the well, and to the detector. The light source is conveniently a light emitting diode capable of emitting a desired wavelength appropriate for the analysis of interest. This particular type of photometric instrument structure is used, for example, not only in Oakton Colorimeter C201 and C401 photometers, but also in Palintest 1000 Chlorometer-Duo photometers, and Hach Pocket Colorimeter II photometers.

Useful filter photometers include an upper housing wall 90 (see FIGS. 2 and 3) likewise provided with a cell chamber or well 62 advantageously provided with an optical window for a light path through the well. In filter photometers, the light source emits a wavelength spectrum that is typically directed across a slit (not shown) and spectral filter (not shown) that select a wavelength appropriate for an analysis of interest.

Similarly, a broad wavelength spectrum is emitted by a light source (not shown) of useful spectrophotometers, and a monochromator (not shown, typically a prism or grid) and one or more slits (not shown) select a wavelength appropriate for an analysis of interest. It will be recognized by one skilled in the photometric art that the foregoing description of useful photometric instruments has been simplified for sake of brevity.

Moreover, useful photometric instruments advantageously store algorithms appropriate for interpreting the data obtained for an analysis of interest, and other data such as blanking data. Photometers such as the Palintest Pooltest 9 photometers, beneficially store a plurality of algorithms specific for a variety of analyses, and include algorithm-selecting touch pads or the like.

In accordance with the invention, suitable photometric cells may be made of glass or plastic, and as demonstrated in Example 2, may be scratched in the optically important region, and in the case of glass cells, may have significant variability in the geometry and quality of the cell glass. Photometric cells having an optical path length of 1 cm or longer such as about 2 cm, are typically particularly advantageous for analysis of a low level of an analyte of interest. On the other hand, an optical path length of 1 cm or less may benefit the analysis of a high level of a particular analyte. In any event, a photometric cell is beneficially properly dimensioned and shaped for a generally mating fit within the cell chamber of a selected photometric instrument.

A particularly beneficial photometric cell is shown in FIG. 8. Advantageously, peripheral wall 156' of a modified photometric cell 150' includes a flange 155', and the photometric cell is dimensioned below the flange to provide two different optical path lengths conveniently provided at about a 90° angle from one another (hidden from view). The optical path length selected depends upon, as indicated in FIG. 8, photometric cell orientation to an optical window alignment mark 80. In a first position of the photometric cell relative to the photometric instrument light path, the photometric cell optical path length is conveniently about 2.2 cm, and in a second position (not shown) which is conveniently at about a 90° angle from the first position, the photometric cell optical path length is conveniently about 1 cm. Photometric cells of this general type (not including a volume-controlling aperture 158') are commercially available from Hach Company. Cells with more than two optical paths lengths may be used.

With continued reference to FIG. 8, a portion of a raised circumferential rim 78 of the modified photometric instrument depicted, is omitted to provide an arcuate guide path bounded by, and defined by, a pair of stops 104 within which flange 155' may be moved, and the photometric cell may thereby be controllably rotated so that contact of the flange with one of the stops advantageously positions one optical path length relative to the photometric instrument light path, whereas approximately 90° photometric cell rotation and contact of the flange with the other stop advantageously positions the other optical path length relative to the photometric instrument light path.

In accordance with a first aspect of a beneficial inventive photometric analysis method, a photometric cell containing a suitable volume of an aqueous sample, is inserted into a cell chamber of a suitable photometer. Alternatively in accordance with a second aspect of a beneficial inventive photometric analysis method, a suitable volume of the aqueous sample is added to a photometric cell disposed in the cell chamber of a suitable photometer. In accordance with a modification of the second aspect, the aqueous sample is added to the cell chamber (or well) of a suitable photometer.

In accordance with the second inventive aspect, the sample is beneficially added to the photometric cell or photometric instrument well, by immersion of at least a portion of the photometric cell or photometric instrument well in an aqueous liquid to be analyzed, and thereafter withdrawing the photometric cell or photometric instrument well from the aqueous liquid. Advantageously, in accordance with the second inventive aspect when a photometric cell is immersed for sample collection, the photometric cell is sealed in the cell chamber to prevent liquid leakage between the cell chamber wall and the exterior of the photometric cell. A water-tight seal may be effected by, for example, use of an O-ring or a suitable adhesive. Adhesion, when used, should be achieved without interfering with the optical window of the cell chamber. An illustrative useful silicone-type adhesive is Napa Brand "Clear RTV Silicone" adhesive sealant distributed by Balkamp, Inc., Indianapolis, Ind.

Advantageously, in accordance with the second inventive aspect, after collection of a sample, the photometric cell or photometric instrument well are leveled as the photometric cell or photometric instrument well is withdrawn from the aqueous liquid. Beneficially, in accordance with the second inventive aspect, the photometer is a waterproof photometer.

When a photometric cell is immersed for sample collection, a peripheral wall of the photometric cell may beneficially be provided with a sample-volume controlling aperture, or the photometric cell may be beneficially dimensioned including having a height selected to capture a desired sample volume. The sample-volume controlling aperture is advantageously sized to allow escape of excess collected sample from the photometric cell, and advantageously located in the peripheral wall at an appropriate height to capture a desired sample volume. Excess liquid is allowed to escape through the aperture to capture a desired sample volume in the photometric cell.

An advantageously sized opening is conveniently 5/16" in diameter. If too small, water surface tension prevents escape of excess liquid. A larger diameter aperture may be used, if desired.

Beneficially, in accordance with the invention when a photometric cell is used, a blank reading is obtained with the photometric cell in the photometer, and the photometric cell remains in the photometer until after the photometric analysis or analyses of interest. After a desired analysis or analyses, the photometric cell may be withdrawn from the photometric instrument. Beneficially, in accordance with the modification when the photometric instrument well is used instead of a photometric cell, a blank reading is likewise obtained prior to analytical agent addition.

With a desired volume of the aqueous sample in the photometric cell or photometer well, when beneficially using a useful reagent delivery device, the delivery end of the reagent delivery device is introduced into the sample to deliver the analytical agent or agents from the reagent delivery device support into the sample, and advantageously a mixing action may be provided, by moving a portion of the support in the sample.

The delivery end may be moved in the sample in a variety of useful ways, with a back-and-forth or up-and-down motion being typically useful. In the case of a small sample volume when use of a microcuvette is beneficial, an up-and-down movement may be practical. For a larger sample volume, other types of motion such as a back-and-forth motion, may be practical or advantageous.

During certain reactions, for example, the conversion of cyanide to cyanogen halide, it is beneficial to minimize introducing air into the aqueous sample. Thus, a mixing action consistent with minimizing interference with a reaction or analysis, should be used when appropriate. Similarly, a gentle motion may be advantageous to avoid sample loss, for example, when using a photometric instrument well such as is illustrated in FIG. 7. Accordingly, in certain instances, a gentle motion may be advantageous; whereas, it may be inappropriate to use vigorous shaking or mixing.

Depending upon the analysis of interest and as appropriate or desired, the delivery end may be continuously immersed in, or repeatedly introduced into, the aqueous sample during the time period provided for contact of the aqueous sample with the reagent delivery device. Typically, the delivery end is continuously immersed. However, for instance, in the case of a small sample volume and use of a microcuvette and an up-and-down motion of the delivery end of the support, an up-and-down motion may prevent continuous immersion, and as a result, a carrier or carriers may be partially or fully withdrawn from the sample during an up stroke and reintroduced into the sample during a down stroke.

Depending upon the analysis of interest and as appropriate or desired, a back-and-forth motion at a gentle rate of about two moves per second may be useful in certain analyses, an up-and-down motion at a gentle rate of one or two up-and-down strokes per second may be useful in certain other analyses, and other types of mixing action and vigorous motion may be appropriate in other analyses. In any event, the type of motion is selected to promote analytical agent delivery into the sample, and advantageously to provide an effective mixing action. The inventive photometric technology, in its broadest aspect, is not constrained by the type of motion selected.

When delivering an analytical agent into an aqueous sample by beneficially using a useful reagent delivery device, the time of contact of the aqueous sample with the reagent delivery device, is selected to provide sufficient time for analytical agent delivery, it being recognized that depending upon the loading of a particular analytical agent and other considerations including the level of analyte and the desired analysis speed, it may not be necessary or desirable for complete analytical agent delivery to be effected. Additional considerations affecting the time of contact include the sample temperature and the analytical agent carrier medium selected. In this regard, a relatively shorter contact time may be used for a carrier medium that delivers an analytical agent relatively more rapidly, whereas a carrier medium that delivers an analytical agent relatively more slowly is benefitted by a relatively longer contact time. For the same contact time, OL 50 and 8S papers may advantageously provide relatively more analytical agent delivery than 404 paper.

For certain analyses when a relatively more rapid analysis speed is desired, a preferred contact time may be less than about one minute, with a shorter contact time in the range of about ten to thirty seconds being commercially highly desirable. If desired or appropriate, a longer contact time may be used. In any event, the inventive photometric technology, in its broadest aspect, is not constrained by the duration of the contact time.

In certain analyses, it may be appropriate or desirable to use more than one reagent delivery device. For example, for total chlorine, all analytical agents may, if desired, be delivered from a common support (see Example 4), or if a free chlorine value is also desired, an iodide salt may be delivered from a second support (see Example 1).

It is not a necessary feature of the inventive photometric technology, in its broadest aspect, that any or all analytical agents be delivered using a reagent delivery device. If appropriate or desired, analytical agent addition in solid or liquid form may precede or follow use of a reagent delivery device. For example, in preparation for a Konig Reaction-based analysis, sodium hypochlorite and phosphate buffer may be added in liquid form to convert cyanide to cyanogen chloride, prior to delivery of Konig reactants from a reagent delivery device. If analytical agent addition follows delivery by a reagent delivery device, withdrawal of the reagent delivery device may, depending upon the particular chemistry, be delayed to allow its use for mixing.

In any event, after an appropriate duration of contact with the sample, a reagent delivery device is withdrawn from the sample. Thereafter, optical development of the liquid may be allowed to continue for an appropriate period of time prior to photometric analysis. Depending upon the analysis of interest and factors including the particular reagents used, the concentration of the reagents in the liquid being analyzed, the final pH, and the sample temperature, optical development of the liquid may continue for up to about two minutes or even up to 20 minutes or more. It will, of course, be recognized that a relatively more rapid optical development and analysis are commercially desirable.

If appropriate, as described in, for instance, Example 7, analysis values may be adjusted to take into consideration any background optical density by repeating the particular methodology but modified by using an appropriate sample free of the analyte of interest.

Blanking of a sample and photometric cell, analytical agent delivery and mixing, and photometric analysis may all be carried out in the same photometric cell. Furthermore, for a photometric cell to remain in a photometer during an entire analysis procedure after its insertion for zeroing the instrument, until its removal after a desired reading or readings, avoids concerns about reproducibility due to photometric cell optical density variability, or smudges or fingerprints or water drops on photometric cells as a result of cell removal and re-insertion.

Throughout this description which includes the Examples that follow, all parts and percentages are weight percent unless otherwise specified.

EXAMPLE 1

Free Chlorine & Total Chlorine

Chlorine analysis has wide commercial applicability, and is useful for testing drinking water, pool and spa water, aquarium water, industrial and environmental water, and for other types of water testing. Medical applicability includes testing of equipment such as dialysis equipment to confirm removal of chlorine and chloramine contaminants. Furthermore, chlorine analysis has applications to food processing. Chlorine can be present in water as free available chlorine and as combined available chlorine. Both forms can be determined together as total available chlorine.

With reference again to reagent delivery device 10 of FIG. 1, in a convenient embodiment, support 12 is made of PVC, is 8 mm wide and has a thickness of 0.009 inches, carrier 16 is ¼" long and 8 mm wide, and carriers 26,36 are each ½" long and 8 mm wide. The carriers are fibrous pads made of Schleicher and Schuell 497 paper, which has a thickness of about 0.2 mm.

¼" long carrier 16 is loaded with approximately ten times the N,N-diethyl-1,4-phenylenediamine (DPD) sulfate used in *Standard Methods for the Examination of Water and Wastewater*, 19th Edition, 1995 (4500-Cl G), which for a 10 ml sample, uses 0.5 ml of a DPD solution containing in the case of anhydrous DPD sulfate, 0.00055 g of the DPD salt. The DPD salt impregnation solution includes 3.4 wt. % of 2,2-bis(hydroxymethyl)propionic acid, as a water soluble barrier-forming agent. The barrier benefit increases when the DPD salt is used in a high loading.

Also described in method 4500-Cl G, is the use of 0.5 ml of a water soluble phosphate buffer solution prepared using an about 2:1 weight ratio of potassium phosphate monobasic anhydrous (4.6 wt. %) to sodium phosphate dibasic anhydrous (2.4 wt. %), to provide a 10 ml sample with a pH in the range of about 6.2 to 6.5. Carriers 26,36 are loaded with potassium phosphate monobasic anhydrous to sodium phosphate dibasic anhydrous in a weight ratio of 23:12 to likewise provide a 10 ml sample with a pH in the range of approximately 6.2 to 6.5. As can be recognized, the DPD sulfate and the phosphate buffer system may be physically separate from one another on the support. The impregnation solution for buffer system carriers 26,36 includes 0.8 wt. % of EDTA.

For free chlorine analysis, 10 ml of a water sample is added to a properly dimensioned photometric cell, and the photometric cell is inserted into a Palintest 1000 Chlorometer-Duo, and the photometer is zeroed. Thereafter, with the photometric cell remaining in the photometer, the delivery end 22 of reagent delivery device 10, is immersed in the sample and moved back and forth for 20 seconds. Immediately thereafter, delivery device 10 is withdrawn from the photometric cell, and the sample color is immediately read for free chlorine. A free chlorine value of 0.05 mg/L is displayed by the photometer.

For total chlorine, a second reagent delivery device (not shown) that includes an iodide salt carrier on a support 12 as previously described, is used. The iodide salt carrier is ¼" long and 8 mm wide, and is impregnated using an impregnation solution containing potassium iodide 99%, and a mixture of 50% PVP k-60 in water (available from ISP Technologies Incorporated, Wayne, N.J.) with 50% methanol, in a weight ratio of 13:15.

After the free chlorine reading, with the photometric cell continuing to remain in the photometer, the delivery end of the second reagent delivery device is introduced into the 10 ml sample and moved back and forth for 20 seconds to deliver the iodide salt and further mix the sample. Immediately thereafter, the second delivery device is withdrawn from the sample, and after a total of three minutes from introducing its delivery end into the sample, the sample color is photometrically read for total chlorine. A total chlorine value of 1.44 mg/L is displayed by the photometer.

Beneficially, as described, the photometric cell remains in the photometer after its insertion for a blank reading in preparation for the free chlorine reading, until its removal after the total chlorine reading.

Advantageously, the inventive technology minimizes manipulations, which reduces the time and labor required for analysis, and provides an optimized blank reading, even when a photometric cell exterior is wet or smudged. Advantageously, delivery of an effective amount of a useful DPD salt into an aqueous sample and accurate photometric analysis of free chlorine may be achieved within one minute of, beneficially about 20 seconds after, introducing the DPD salt-bearing portion of the support into the sample.

In a useful modification of reagent delivery device 10, fibrous pad 16 and the propionic acid are not used, and instead, support 12 carries a mass of 0.0165 g DPD sulfate, and carriers 26,36. The DPD sulfate mass is deposited on the support from a solution of 1.176 g DPD sulfate in 0.838 g deionized water and 0.40 g methanol.

In another useful modification, fibrous pad 16 is omitted, and the support carries a mass that is a mixture of DPD sulfate and the propionic acid, and as before, carriers 26,36.

The mass is deposited from a solution that includes 9.8 wt. % of the propionic acid, and that provides a loading on the support of 0.0164 g DPD sulfate, with a ratio of the DPD sulfate to the propionic acid of about 5:1. Following the previously described method but using a different water sample and wiping the outside of a properly dimensioned photometric cell to be clean and dry prior to insertion into a Hach Pocket Colorimeter II, and using this modification of reagent delivery device 10, a free chlorine value of 1.82 mg/L is displayed by the photometer.

According to US EPA accepted standard methodology, a water sample size of 10 ml is used for chlorine analysis. Other sample sizes may, if desired, be used. For example, a 25 ml sample may be used.

The reacted photometry samples are free of undissolved solids and marked by clarity.

Consideration must be given to higher sample temperatures increasing the tendency for chloramines to react and hence interfering with accurate free chlorine analysis, and to higher temperatures increasing color fading.

EXAMPLE 2

Scratched Photometric Cells

This Example demonstrates that the inventive photometric technology beneficially substantially eliminates variations in data resulting from optical variability of photometric cells.

With reference to FIGS. 2 and 3, a multiwavelength photometer 60 is shown. Conveniently, photometer 60 is an Palintest Pooltest 9 photometer. Photometric instrument 60 beneficially includes a cell chamber 62 for receiving a photometric cell 50 for optical analysis, an ON touch pad 64, an OFF touch pad 65, a display 68, a touch pad 70 for zeroing the instrument and for display of optical readings, and a slide switch 76 for selecting a 520 nm or 570 nm wavelength. A photometric cell holding chamber 63 is not needed in the inventive methodology. A touch pad 66 when used to activate the SYSTEM mode, beneficially allows system options such as displaying mg/L or ppm.

Photometric instrument 60 also beneficially includes a plurality of touch pads 82 each for selecting a desired analysis, including, but not limited to, as marked in FIGS. 2 and 3, for free chlorine analysis (marked "$Cl_2^F$"), total chlorine analysis (marked "$Cl_2^T$"), bromine analysis (marked "$Br_2$"), ozone analysis (marked "$O_3$"), copper analysis (marked "Cu"), pH analysis (marked "pH"), total alkalinity analysis (marked "Alk"), and calcium hardness analysis (marked "Cal"). Also shown in FIGS. 2 and 3 are touch pads 84 inoperative for the Pooltest 9 instrument.

For free chlorine analysis, the instrument is turned ON using touch pad 64, slide switch 76 is positioned to select a 520 nm wavelength, and the appropriate touch pad 82 for selecting free chlorine analysis, is pressed. Three appropriately dimensioned, generally cylindrical photometric cells 50 are selected, one of which is made of light transmissive plastic and two of which are made of light transmissive glass. 10 ml of tap water is added to each photometric cell.

The plastic cell is inserted into cell chamber 62 and photometer 60 is zeroed by pressing touch pad 70. Thereafter, the plastic cell is removed from cell chamber 62 and capped, then intentionally scratched using a belt sander in the optically important region, then re-inserted in cell chamber 62, and rotated using ⅙th turns to obtain six readings by repeatedly pressing touch pad 70. The readings reveal an average elevated optical value of 0.48 ppm from scratching of the plastic cell.

Thereafter, one of the glass cells (glass cell #1) is inserted into cell chamber 62 and photometer 60 is zeroed. Then, glass cell #1 is removed from cell chamber 62 and capped, then intentionally scratched using a belt sander in the optically important region, then re-inserted in cell chamber 62, and rotated using ⅙th turns to obtain six readings by repeatedly pressing touch pad 70. The readings reveal an average elevated optical value of 0.34 ppm from scratching of glass cell #1.

Thereafter, the other glass cell (glass cell #2), which likewise contains 10 ml of tap water, is inserted into cell chamber 62 and photometer 60 is zeroed. Glass cell #2 is then rotated using ⅙th turns to obtain six readings by repeatedly pressing touch pad 70. The readings average 0.00 ppm and thus show no elevated optical value.

After pouring out the tap water from the three photometric cells, 10 ml of an identical free chlorine-containing aqueous sample is added to each photometric cell. The plastic cell containing the aqueous sample is reinserted into cell chamber 62, and after zeroing photometer 60 using touch pad 70, the delivery end of reagent delivery device 10 described in Example 1, is introduced into the 10 ml sample, and gently moved back and forth for 20 seconds to deliver the phosphate buffer system and DPD sulfate into the sample, and beneficially provide a mixing action. Immediately thereafter, reagent delivery device 10 is withdrawn from the plastic cell, and the color of the liquid in the plastic cell is read for free chlorine by pressing touch pad 70. A free chlorine value of 0.59 ppm is shown by display 68.

This procedure is repeated for the free chlorine-containing aqueous sample in glass cell #1 and for the free chlorine-containing aqueous sample in glass cell #2. Free chlorine values of 0.62 ppm (glass cell #1 sample) and 0.59 ppm (glass cell #2 sample) are shown by display 68. These data demonstrate that the inventive methodology beneficially substantially eliminates variations in data resulting from optical variability of photometric cells.

Immediately after obtaining the reading for the liquid in glass cell #2, and using the blanking data stored by the photometer for glass cell #2, the liquid-containing plastic cell and then liquid-containing glass cell #1 are re-inserted into cell chamber 62, and free chlorine values of 1.14 ppm (plastic cell sample) and 0.90 ppm (glass cell #1 sample) are shown by display 68, by pressing touch pad 70. Adjusting these values by subtracting the average elevated optical values earlier obtained, yields results as follows: 0.66 ppm (1.14 ppm-0.48 ppm) for the plastic cell sample, and 0.56 ppm (0.90 ppm-0.34 ppm) for the glass cell #1 sample. These additional results confirm that the inventive methodology substantially eliminates variations in data resulting from optical variability of photometric cells.

Furthermore, from this Example, it can be recognized by one skilled in the photometry art, that when using the inventive methodology, matched cells are not required, and scratched photometric cells are functional and need not be discarded.

EXAMPLE 3

Waterproof Photometer

With reference to FIGS. 4 and 5, a waterproof photometer 160 is shown. Conveniently, photometer 160 is an Oakton Colorimeter C201. The photometric instrument includes power button 64, mode touch pad 66, display 68, a touch pad 72 for zeroing the photometer, and a touch pad 74 for entry of the selected mode and display of optical readings. The C201 instrument provides for analysis of free chlorine and total chlorine, using a wavelength of 525 nm. The analysis desired is selected using mode touch pad 66 to select an appropriate algorithm. Beneficially for the inventive methodology of this Example, cell chamber 62 of the C201 instrument is located near an end 86 of the instrument. The C201 instrument further includes optical window alignment mark 80.

An appropriately dimensioned plastic photometric cell 150 is friction fit in cell chamber 62 of waterproof photometer 160, and, without interfering with the optical window of the cell chamber, sealed in the cell chamber using an adhesive sealant commercially sold as Napa Brand "Clear RTV Silicone" distributed by Balkamp, Inc., Indianapolis, Ind. Photometric cell 150 is beneficially dimensioned, when filled to cell rim 154, to capture a 10 ml volume.

An approximately twelve quart plastic basin is partially filled with tap water, and 5% sodium hypochlorite solution is added to the tap water to provide a free chlorine level of approximately 5 ppm. Thereafter, approximately 2 pounds of cherry tomatoes are added to the chlorine solution in the basin and washed with the chlorine solution. Then, with the cherry tomatoes in the basin, and referring in particular to FIG. 4, after turning on the photometer using power button 64 and selecting free chlorine analysis using mode touch pad 66 and pressing touch pad 74 to enter the selected mode, photometric cell 150 is immersed beneath the surface of the chlorine solution at a convenient angle, and then as the photometric cell is withdrawn from the chlorine solution, leveled. After the photometric cell and photometer end 86 are withdrawn from the chlorine solution and leveled, the photometer is zeroed using touch pad 72, with a blank reading of 0.00 ppm shown by display 68.

Thereafter, referring in particular to FIG. 5, the delivery end of reagent delivery device 10 described in Example 1 for free chlorine analysis, is introduced into the 10 ml sample captured by photometric cell 150, and gently moved back and forth for 20 seconds to deliver the analytical agents from a common support into the sample, and beneficially provide a mixing action. Immediately thereafter, reagent delivery device 10 is withdrawn from the photometric cell, and the color of the liquid within photometric cell 150 is immediately read for free chlorine by pressing touch pad 74. A free chlorine value of 4.5 ppm is shown by display 68.

Photometric cell 150 is rinsed using tap water, and after approximately 5 to 6 minutes, again referring in particular to FIG. 4, the photometric cell is immersed beneath the surface of the chlorine solution at a convenient angle, and then as the photometric cell and photometer end 86 are withdrawn from the chlorine solution, leveled. Repetition of the remainder of the described method, reveals a free chlorine value of 4.2 ppm.

Provided that obtaining a particular desired sample volume is not prevented and the sample is within the optical window, the photometric cell rim may extend further above raised circumferential rim 78 (omitted for simplification from FIG. 4) than is shown in FIG. 5, of cell chamber 62.

EXAMPLE 4

Photometer Well for Sample Collection

With reference to FIG. 7 and a reagent delivery device 20 useful for pH analysis, in a convenient embodiment, the device support is made of PVC, is 6.5 mm wide and has a thickness of 0.009 inches. Affixed to the opposing faces of the support are fibrous pads made of Schleicher and Schuell 404 paper, which has a thickness of approximately 0.2 mm, a water absorbency value of 1.4 g/100 cm$^2$, and a basis weight of approximately 80 g/cm$^2$. On each face of the support is a ¼" long and 6.5 mm wide fibrous pad, and a 1" long and 6.5 mm wide fibrous pad. Conveniently, the ¼" long pads are located closer than the 1" long pads to the delivery end of the support.

The ¼" long pads are prepared by impregnating S&S 404 paper using a 13 wt. % solution of sodium thiosulfate (99%) in deionized water, adjusted to a pH of approximately 7.0. The 1" long pads are prepared by impregnating S&S 404 paper using a 50:50 (on a weight basis) methanol to deionized water impregnation solution containing 1.7 wt. % phenol red (sodium salt), 1.5 wt. % sodium thiosulfate and 1 wt. % potassium chloride, adjusted to a pH of approximately 7.8.

With reference to FIGS. 6 and 7, a waterproof photometer 160' is shown. Conveniently, photometer 160' is an Oakton Colorimeter C401. As in the case of the C201 instrument, the C401 instrument includes power button 64, mode touch pad 66, display 68, touch pad 72 for zeroing the photometer, and touch pad 74 for entry of the selected mode and display of analytical readings. The C401 instrument beneficially provides for analysis of free chlorine, total chlorine, pH and cyanuric acid, using a wavelength of 525 nm. The particular analysis desired is selected using mode touch pad 66 to select an appropriate algorithm.

Beneficially for the inventive methodology of this Example, cell chamber 62 (or well) of the C401 instrument is located near an end 86 of the instrument. Optical window alignment mark 80 (shown in FIG. 7) is not needed for this particular Example. Referring also to FIG. 10, well 62, when filled to raised circumferential rim 78 (shown only in FIGS. 7 and 10), contains approximately 22 ml.

A sample of pool water is taken from Laurel Creek Swimming Pool, Rock Hill, S.C., and determined using a pH meter to have a pH of 7.78. The pH meter is a microcomputer pH/mV/TEMP meter #6171 available from Jenco Instruments, Inc., San Diego, Calif.

An approximately twelve quart plastic basin is partially filled with the pool water, and after turning on the photometer using power button 64 and selecting pH analysis using mode touch pad 66 and pressing touch pad 74 to enter the selected mode, well 62 is twice immersed beneath the surface of the pool water, filled, withdrawn from the pool water, and emptied to rinse the well. Then, referring in particular to FIG. 6, well 62 is immersed beneath the surface of the pool water at a convenient angle, and then referring in particular to FIG. 10, as the well is withdrawn from the pool water, leveled. With continued reference in particular to FIG. 10, after the well and photometer end 86 are withdrawn from the pool water and leveled, the photometer is zeroed using touch pad 72, with a blank reading of 0.0 pH shown by display 68.

Thereafter, referring in particular to FIG. 7, the delivery end of reagent delivery device 20 is introduced into the approximately 22 ml sample within well 62, and moved gently back and forth for 20 seconds to deliver the analytical agents from a common support into the sample, and beneficially provide a mixing action. Immediately thereafter, reagent delivery device 20 is withdrawn from the well, and referring again in particular to FIG. 10, the pH of the liquid within the well is determined by pressing touch pad 74. A pH value of 7.7 is shown by display 68.

With the same pool water, repeat of the methodology just described using a fresh reagent delivery device 20, results in a pH value of 7.8 shown by display 68.

EXAMPLE 5

Waterproof Photometer in Direct Sun Light

Referring to FIGS. 8 & 9, an appropriately dimensioned plastic photometric cell 150' that includes a peripheral wall 156' provided with a sample volume-controlling aperture 158', is friction fit in cell chamber 62 of waterproof photometer 160', which as described in Example 4, is an Oakton Colorimeter C401. To allow escape of excess sample from the photometric cell, aperture 158' is conveniently approximately 5/16 inch in diameter.

Advantageously, as indicated in FIG. 8, the photometric cell is dimensioned to provide two different optical path lengths conveniently provided at approximately a 90° angle from one another (hidden from view). The optical path length selected depends upon, as indicated in FIG. 8, photometric cell orientation to optical window alignment mark 80. In a first position shown in FIGS. 8 and 9, a photometric cell optical path length of 2.2 cm is selected. In a second position (not shown) which is conveniently at approximately a 90° angle from the first position, the photometric cell optical path length selected is 1 cm. Beneficially, as previously described, cell chamber 62 of the C401 instrument is located near an end 86 of the instrument.

A suitably sized container is partially filled with a prepared pool water matrix that contains total chlorine. In like manner as shown in FIGS. 4 and 6, but in direct sun light, after turning on the photometer using power button 64 and selecting total chlorine analysis using mode touch pad 66 and pressing touch pad 74 to enter the selected mode, photometric cell 150' is immersed beneath the surface of the pool water matrix at a convenient angle for collecting a sample. Volume-selecting aperture 158' is located in peripheral wall 156' at an appropriate height to capture a 10 ml sample volume after excess sample escapes from the photometric cell through the aperture.

After the photometric cell is sufficiently filled, the photometric cell and photometer end 86 are withdrawn from the pool water matrix, the photometer is leveled, and excess sample is allowed to escape through aperture 158', and, referring in particular to FIG. 8, with a generally cylindrical, appropriately dimensioned, excess stray light-blocking cap 88 covering the photometric cell, the photometer is zeroed in direct sun light using touch pad 72. When it is attempted to zero the photometer in direct sun light without cap 88 covering the photometric cell, display 68 gives an error message according to which excess stray light is detected.

Thereafter, referring again to FIG. 9, with stray light-blocking cap 88 removed, the delivery end of a total chlorine analysis, reagent delivery device 40 useful in the present invention, is introduced into the 10 ml pool water matrix sample and moved gently back and forth for 20 seconds to deliver a phosphate buffer system, DPD sulfate and potassium iodide from a common support into the sample, and beneficially provide a mixing action. Reagent delivery device 40 corresponds to reagent delivery device 10 described in Example 1, with the potassium iodide-impregnated pad also described in Example 1 affixed to support 12.

Immediately thereafter, reagent delivery device 40 is withdrawn from the photometric cell, and referring again to FIG. 8, the photometric cell is covered with cap 88, and the color of the liquid within the photometric cell is analyzed in direct sun light, after a three minute waiting period, for total chlorine by pressing touch pad 74. A total chlorine value of 0.99 mg/L is shown by display 68. When it is attempted to obtain a total chlorine reading in direct sun light without cap 88 covering the photometric cell, display 68 again gives an error message according to which excess stray light is detected.

Photometric cell 150' is rotatable in cell chamber 62 for selecting a longer or shorter optical path length, of benefit for instance when an over-range reading is found using the longer path length. Beneficially, with reference to FIG. 8, modified photometric cell 150' includes flange 155', and a portion of a raised circumferential rim 78 of the modified photometric instrument is omitted to provide an arcuate guide path bounded by, and defined by, a pair of stops 104 within which flange 155' may be moved and the photometric cell may thereby be controllably rotated so that advantageously flange contact with one of the stops positions one optical path length relative to the photometric instrument light path, whereas flange contact with the other stop positions the other optical path length relative to the photometric instrument light path.

EXAMPLE 6

Turbidimetric Analysis-Cyanuric Acid

Following the procedure of Example 5 but using a suitably sized container partially filled with pool water taken from Laurel Creek Swimming Pool, Rock Hill, S.C., cyanuric acid analysis is selected using mode touch pad 66 and pressing touch pad 74, and a 10 ml pool water sample is collected by, as before, immersion of photometric cell 150' and end 86 of a waterproof Oakton Colorimeter C401. Prior to collecting the sample, photometric cell 150' is rinsed twice with the pool water. Thereafter, referring again to FIG. 8, with cap 88 covering the photometric cell, touch pad 72 is pressed to zero photometer 160', and display 68 reads 0 ppm.

Thereafter, with cap 88 removed, 10 drops of a solution of 1.3 wt. % melamine in propylene glycol/distilled water (15:1 weight basis ratio) are added to the 10 ml pool water sample, and referring again to FIG. 9, immediately thereafter the delivery end of a reagent delivery device useful for cyanuric acid analysis (not shown in FIG. 9), is introduced into the liquid and moved gently back and forth for 20 seconds to deliver a buffer system, and beneficially provide a mixing action. The formation of a fine white suspension occurs. After the 20 seconds contact time, the reagent delivery device is withdrawn from the liquid, and after waiting 10 seconds, with cap 88 covering photometric cell 150', touch pad 74 is pressed to display a cyanuric acid value of 27 ppm.

The reagent delivery device in a convenient embodiment, includes a support made of PVC, is 8 mm wide, and has a thickness of 0.009 inches. Affixed to both faces of the support are fibrous pads made of S&S 8S paper. Each pad is 1" long and 8 mm wide. The pad is prepared by impregnating S&S 8S paper using a solution of 15.6 wt. % tris (hydroxymethyl)aminomethane hydrochloride and 5.1 wt. % boric acid in deionized water.

EXAMPLE 7

Konig Reaction-Based Analyses

Certain beneficial methods for photometric analysis that rely upon the evaluation of liquid color, are based upon the Konig Reaction. In these analyses, a cyanogen halide reacts with a cyanogen halide-reactive pyridine compound to produce a Konig Reaction intermediate that reacts with a barbituric acid compound to yield a calorimetrically analyzable, colored complex. Pyridine, pyridinium salts such as pyridinium trifluoroacetate, and pyridine derivatives such as γ-picoline (4-methylpyridine), nicotinic acid and isonicotinic acid (4-pyridinecarboxylic acid), nicotinamide, and pyridine-3-nitrophthalic acid, are exemplary of pyridine compounds described as useful in the Konig Reaction. Barbituric acid, barbituric acid derivatives such as 1,3-dimethylbarbituric acid ("1,3-DMB"), and thiobarbituric acid derivatives such as 1,3-diethyl-2-thiobarbituric acid exemplify color-forming barbituric acid compounds described as useful in the Konig Reaction.

Depending upon the particular color-forming chemistry, the photometrically analyzable, colored complex produced by the Konig Reaction, varies in color, and accordingly an appropriate wavelength for photometric analysis varies.

Konig Reaction-based analyses described in the prior art include, but are not limited to, cyanide analysis, chlorine analysis, and analysis of nicotine metabolites. Chloramine-T, N-chlorosuccinimide/succinimide, and sodium hypochlorite exemplify prior art chlorinating reagents for converting cyanide to cyanogen chloride for cyanide analysis. Similarly, for chlorine analysis, chlorine can be reacted with a water soluble alkali metal cyanide to produce a cyanogen chloride to be reacted with Konig reagents. Likewise, nicotine metabolites may be reacted with a color-forming barbituric acid compound.

Cyanide can be present in various forms in water. A particular concern is free cyanide ion. In drinking water, at high doses, this form of cyanide inhibits cellular respiration and can result in death. Because of the toxicity to humans, the U.S. EPA has set 0.2 mg/L as the maximum concentration that can be present in drinking water. Sodium cyanide, potassium cyanide and certain other cyanide salts, release cyanide ion when dissolved in water. The usefulness of cyanide analysis is not limited to drinking water, but rather has wide applicability including to plant material, food, blood chemistry, and to many different industrial processes including to industrial wastewater.

With reference to a reagent delivery device 10' of FIG. 12 for cyanide analysis, in a convenient embodiment, support 12 is made of PVC, is 8 mm wide and has a thickness of 0.009 inches, and carriers 16',26" are each ½" long and 8 mm wide. Carriers 16',26' are fibrous pads made of Schleicher and Schuell (S&S) 404 paper, and are attached is near support end 22 by double-faced adhesive to face 14 of the support. To prepare pad 16', a 13 wt. % solution of chloramine-T hydrate in deionized water having a pH of 9.7, is used to impregnate S&S 404 paper. To prepare pad 26', a solution of 32.9 wt. % sodium phosphate monobasic and 5.6 wt. % sodium phosphate dibasic in deionized water having a pH of 4.7, is used to impregnate S&S 404 paper. S&S 404 paper has a thickness of approximately 0.2 mm, a water absorbency value of 1.4 g/100 cm$^2$, and a basis weight of approximately 80 g/cm$^2$.

Figure 13:
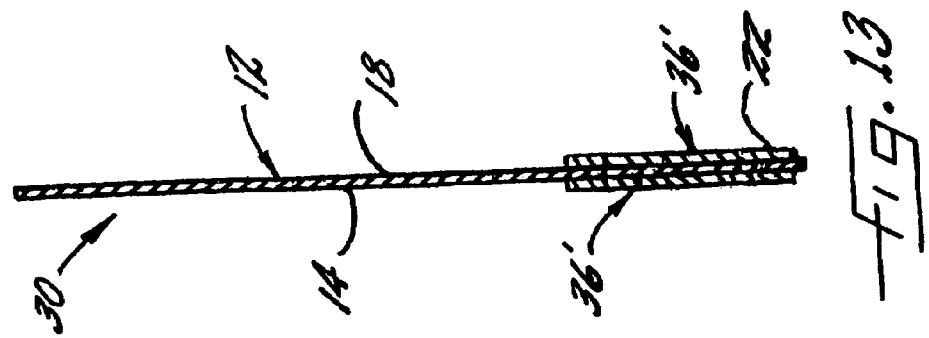

With reference to reagent delivery device 30 of FIG. 13, in a convenient embodiment, support 12 is as previously described with reference to device 10', and carriers 36' are each 1" long and 8 mm wide. Carriers 36' are fibrous pads made of Schleicher and Schuell (S&S) 404 paper, and are attached near support end 22 by double-faced adhesive to opposite faces 14,18 of the support. To prepare pads 36', a solution of 12.8 wt. % 1,3-dimethylbarbituric acid, 14.4 wt. % isonicotinic acid and 5.7 wt. % sodium hydroxide having a pH of 6.4, is used to impregnate S&S 404 paper.

A cyanide standard (sodium cyanide) having a concentration of approximately 0.5 ppm cyanide, is prepared using water free of chlorine and cyanide. The pH is adjusted to 11 using sodium hydroxide solution.

Figure 14:
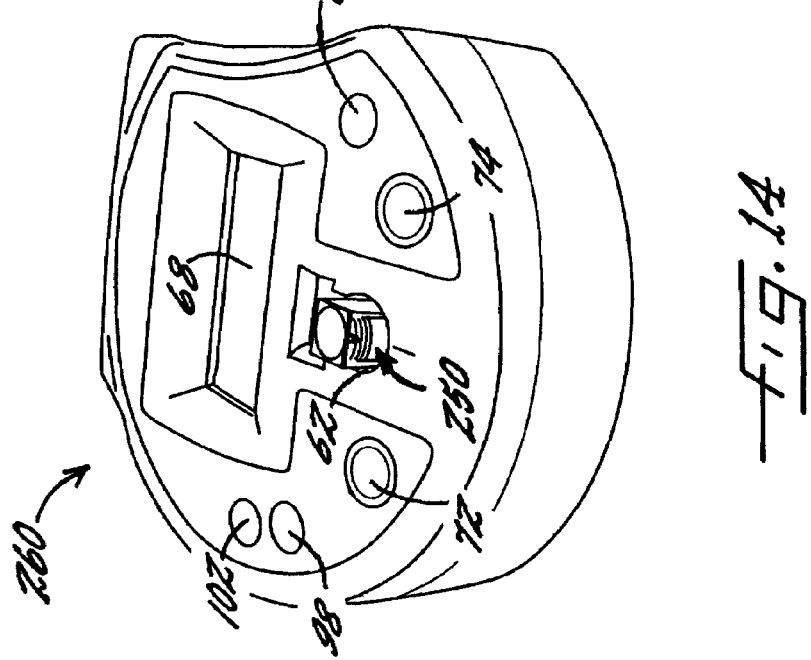
FIG. 14 is a perspective view of another useful photometric instrument, with a suitable microcuvette inserted in the cell chamber.

2 ml of the cyanide standard at a temperature of approximately 72° C., is added to a microcuvette 250, and the outside of microcuvette 250 is wiped to be clean and dry. Referring particularly to FIG. 14, the microcuvette is then inserted into cell chamber 62 of a CO7500 Colorimeter using a mark 252 (especially see FIG. 15) as a guide, and photometer 260 is zeroed. A wavelength of 590 nm is used.

Beneficial photometer features include power button 64, display 68, touch pad 72 for zeroing the photometer, a touch pad 74 for display of analytical readings, a touch pad 98 for continuous readout of changes in absorbance, and a touch pad 102 for selecting whether percent transmission or optical density is displayed, Thereafter, with microcuvette 250 remaining in photometer 260, the delivery end of reagent delivery device 10' of FIG. 12, is dipped in the 2 ml cyanide standard for 30 seconds to repeatedly immerse carrier pads 16',26' so that the pH is appropriately buffered and cyanide is converted to cyanogen chloride. An up-and-down motion of reagent delivery device 10' is used to deliver the analytical agents from pads 16',26' and provide a mixing action. The up-and-down motion is at a gentle constant rate of approximately one up-and-down motion per second.

Immediately after 30 seconds contact time with the 2 ml volume of cyanide standard, device 10' is withdrawn from the microcuvette, and referring particularly to FIG. 15, beginning within 10 seconds, the delivery end of reagent delivery device 30 is dipped in the liquid in the microcuvette for 30 seconds to repeatedly immerse carrier pads 36'. As before, an up-and-down motion at a gentle constant rate of approximately one up-and-down motion per second, is used to deliver the analytical agents from pads 36' and provide mixing.

Immediately after 30 seconds contact time with the liquid in the microcuvette, device 30 is withdrawn from the microcuvette. After allowing color development of the liquid in the microcuvette for 3, 5 and 10 minutes from withdrawal of reagent device 30, the color of the liquid in the microcuvette is photometrically evaluated, and the respective optical density readings are as follows: 0.28, 0.42 and 0.63. The increase in optical density from the 3 minute to the 10 minute interval, indicates continuation of the color development. A final pH of 6.8 is measured after the 10 minute interval.

As described, the microcuvette remains in the photometer during an entire analysis procedure after insertion for zeroing the instrument, until removal after a desired reading or readings. Even so, when highly accurate readings are desired, background optical density needs to be taken into account. Repeat of the method of this Example but modified by using 2 ml of a water sample free of cyanide, reveals 3 and 5 minute background optical density readings as follows: 0.10 and 0.10. Adjustment for the background optical density yields 3 and 5 minute optical density readings as follows: 0.18 (0.28-0.10) and 0.32 (0.42-0.10).

Beneficially, cyanide reacts with a halogenating agent in an acidic reaction environment to yield a cyanogen halide such as cyanogen chloride. The halogenating reaction environment pH is believed to be significant not only in regard to promoting complete and rapid conversion of cyanide to cyanogen halide but also for minimizing cyanogen halide degradation. An advantageous reaction environment acidity for the halogenating reaction is an elevated acidic pH significantly greater than pH 2, beneficially in the range of from about 3 to less than 7, preferably about 5 to 6 to promote rapid conversion of cyanide to cyanogen halide and minimize cyanogen halide degradation. A reaction environment pH for the halogenating reaction greater than 7.5, is typically detrimental.

Likewise, the reaction environment pH for reaction of the Konig reagents with a cyanogen halide to produce a photometrically analyzable, colored complex is significant for optimum color development and speed of color development. In this regard, an advantageous final pH for a Konig Reaction is an elevated pH significantly greater than pH 3, beneficially in the range of from about pH 4 to 7.5 depending upon the particular Konig Reaction-based analysis, the Konig reagents selected and the buffer selected. A final pH substantially below 4 or substantially in excess of pH 7.5 is typically detrimental for optimum color development and speed of color development.

In accordance with preferred reagent delivery device 10', support 12 thereof carries, and delivers into a liquid to be analyzed, an effective amount of a suitable water soluble buffer for controlling the reaction environment pH for the halogenating reaction and the reaction environment pH for the Konig Reaction to each be an appropriate elevated pH. Beneficial water soluble buffers are known in the prior art, and include, but are not limited to, phosphate and acetate buffers, including modified phosphate buffers.

Although a smaller sample volume may be used, a preferred sample volume for cyanide analysis is about 2 ml or less. A greater sample volume may, if desired, be used; however, as sample volume is increased, considerations such as increased reagent amounts should be taken into account to maintain maximum color development in the desired period of time.

Sample pH should be known or determined, and if not acceptable, the sample pH should be appropriately adjusted. A sample pH in the range of about 5 to 11, is typically preferred for this beneficial cyanide analysis.

EXAMPLE 8

Turbidimetric Analysis-Calcium Hardness

A reagent delivery device for calcium hardness analysis, in a convenient embodiment, includes a support made of PVC, is 5.5 mm wide, and has a thickness of 0.009 inches. Affixed to a face of the support is a fibrous pad made of S&S 8S paper. The pad is ½" long and 5.5 mm wide. The pad is prepared by impregnating S&S 8S paper using a solution of 13.6 wt. % ammonium oxalate in deionized water. The oxalate salt impregnation solution includes 3.0 wt. % of 2,2-bis(hydroxymethyl)propionic acid (98%), as a water soluble barrier-forming agent.

With reference again to the CO7500 Colorimeter of FIGS. 14 and 15, 2 ml of a sample of pool water taken from Laurel Creek Swimming Pool, Rock Hill, S.C. is added to a microcuvette 250, and the microcuvette is then inserted into cell chamber 62, and photometer 260 is zeroed using touch pad 72. A wavelength of 590 nm is conveniently used.

Thereafter, with the microcuvette remaining in photometer 260, the delivery end of the calcium hardness reagent delivery device, is dipped in the 2 ml sample with a gentle up-and-down motion for 20 seconds. The formation of a fine suspension occurs. After the 20 seconds contact time, the reagent delivery device is withdrawn from the sample, and immediately touch pad 74 is pressed to display the optical density of the liquid in the microcuvette. The optical density is 0.54, which according to a standard curve, is equivalent to a calcium hardness value of 52 ppm.

EXAMPLE 9

Ammonia Analysis

Referring to FIG. 11, a reagent delivery device 110 for ammonia analysis, in a convenient embodiment, includes a support 12 made of PVC, is 8 mm wide, and has a thickness of 0.009 inches. Affixed to a first face 14 of the support are spaced apart fibrous pads 116,136 made of S&S 404 paper and S&S 593 paper, respectively, and of ¼" length and ½" length, respectively. Fibrous pad 116 is prepared by impregnating S&S 404 paper using a solution of 20 wt. % dichloroisocyanuric acid sodium salt in deionized water. Fibrous pad 136 is prepared by impregnating S&S 593 paper using a solution of 24 wt. % sodium nitroferricyanide (III) dihydrate (99%) and 10.3 wt. % salicylic acid sodium salt in deionized water. S&S 593 paper is a cellulosic paper having a thickness of 0.36 mm and a water absorbency value of 2.75 g/100 cm$^2$.

Affixed to opposite support face 18 is a 1" long fibrous pad 126. Fibrous pad 126 is prepared by impregnating S&S 593 paper using a solution of 21 wt. % potassium hydroxide and 43 wt. % 50% sodium hydroxide in deionized water/methanol (0.8:1 weight basis ratio). All three pads are 8 mm wide.

With reference again to the CO7500 Colorimeter of FIGS. 14 and 15, 2 ml of a sample of aquarium water spiked with approximately 0.3 ppm ammonia, is added to microcuvette 250, and the microcuvette is then inserted into cell chamber 62, and photometer 260 is zeroed using touch pad 72. A wavelength of 680 nm is conveniently used.

Thereafter, with the microcuvette remaining in photometer 260, delivery end 122 of reagent delivery device 110, is dipped in the 2 ml sample with a gentle up-and-down motion for 30 seconds. After the 30 seconds contact time, the reagent delivery device is withdrawn from the sample, and after a waiting period of 3 minutes, touch pad 74 is pressed to display the optical density of the liquid in the microcuvette. The optical density is 0.27.

EXAMPLE 10

Bromine Analysis

With reference again to FIGS. 2 and 3 and photometer 60, the photometer is turned ON using touch pad 64, slide switch 76 is positioned to select a 520 nm wavelength, and the appropriate touch pad 82 for selecting bromine analysis, is pressed. 10 ml of a prepared pool water matrix containing 0 ppm bromine (initial pH 7.5, initial temperature of 74° F.) is added to an appropriately dimensioned, generally cylindrical plastic photometric cell 50, the photometric cell is positioned in cell chamber 62, and photometer 60 is zeroed. Thereafter, the delivery end of reagent delivery device 10 described in Example 1, is introduced into the 10 ml sample, and gently moved back and forth for 20 seconds. Immediately thereafter, reagent delivery device 10 is withdrawn from the plastic cell, and the color of the liquid in the plastic cell is read for bromine by pressing touch pad 70. A bromine value of 0.01 ppm is shown by display 68. The final pH is 6.3.

Repeat the described method using 10 ml of the pool water matrix containing approximately 2 ppm bromine (initial pH 7.4, initial temperature of 75° F.), results in a bromine value of 2.30.

EXAMPLE 11

Free Copper Analysis

With reference again to FIG. 2 and photometer 60, the photometer is turned ON using touch pad 64, slide switch 76 is positioned to select a 520 nm wavelength, and the appropriate touch pad 82 for selecting copper analysis, is pressed.

10 ml of a prepared pool water matrix containing 0 ppm copper (initial pH 7.5, initial temperature of 75° F.) is added to an appropriately dimensioned, generally cylindrical glass photometric cell 50, the photometric cell is positioned in cell chamber 62, and photometer 60 is zeroed. Thereafter, as in FIG. 3, the delivery end of a reagent delivery device for free copper analysis of like appearance to device 30 of FIG. 13, is introduced into the 10 ml sample, and gently moved back and forth for 20 seconds. Immediately thereafter, the reagent delivery device is withdrawn from the glass cell, and the color of the liquid in the glass cell is read for free copper by pressing touch pad 70. A value of 0.00 ppm is shown by display 68. The final pH is 6.9.

Repeat of the described method using 10 ml of the pool water matrix containing approximately 1 ppm free copper (initial pH 7.5, initial temperature of 75° F.), results in a free copper value of 1.05. The final pH is 6.7.

The reagent delivery device for copper analysis, in a convenient embodiment, includes a support made of PVC, is 8 mm wide, and has a thickness of 0.009 inches. Affixed to opposing faces of the support are fibrous pads made of S&S 404 paper. Each pad is 1" long and 8 mm wide. The pads are prepared by impregnating S&S 404 paper using a solution of 8 wt. % 4,4'-dicarboxy-2,2'-biquinolone potassium salt and 5.5 wt. % sodium metabisulfite in distilled water/ethanol (27:1 weight basis ratio), adjusted to a pH of 6.5.

EXAMPLE 12

Total Alkalinity Analysis

With reference again to FIG. 2 and photometer 60, the photometer is turned ON using touch pad 64, slide switch 76 is positioned to select a 570 nm wavelength, and the appropriate touch pad 82 for selecting total alkalinity analysis, is pressed.

10 ml of a prepared pool water matrix containing approximately 120 ppm total alkalinity (initial pH 7.6, initial temperature of 73° F.) is added to an appropriately dimensioned, generally cylindrical glass photometric cell 50, the photometric cell is positioned in cell chamber 62, and photometer 60 is zeroed. Thereafter, as in FIG. 3, the delivery end of a reagent delivery device for total alkalinity analysis of like appearance to device 30 of FIG. 13, is introduced into the 10 ml sample, and gently moved back and forth for 20 seconds. Immediately thereafter, the reagent delivery device is withdrawn from the glass cell, and the color of the liquid in the glass cell is read for total alkalinity by pressing touch pad 70. A value of 105 ppm is shown by display 68. The final pH is 3.9.

The reagent delivery device for total alkalinity analysis, in a convenient embodiment, includes a support made of PVC, is 8 mm wide, and has a thickness of 0.009 inches. Affixed to the opposing faces of the support are 1" long fibrous pads made of S&S 404 paper. Each pad is 8 mm wide. The pads are prepared by impregnating S&S 404 paper using a solution of 0.72 wt. % bromocresol green sodium salt, 18.93 wt. % glutaric acid, and 3.69 wt. % glycine in deionized water/methanol (1.3:1 weight basis ratio), adjusted to a pH of 3.5.

The present invention may be carried out with various modifications without departing from the spirit or essential attributes thereof. Accordingly, reference should be made to the appended claims, rather than to the foregoing specification as indicating the scope of the invention.

The invention claimed is:

1. A photometric analytical method comprising
    disposing a photometric cell containing an aqueous sample to be analyzed, in a photometric instrument;
    obtaining a blank reading;
    then moving a portion of a support of a reagent delivery device in said aqueous sample wherein said photometric cell remains disposed in said photometric instrument, to deliver from the reagent delivery device support into said aqueous sample an effective amount of at least one water soluble analytical agent for photometric analysis, and also to provide a mixing action;
    thereafter withdrawing said reagent delivery device from the resulting liquid in said photometric cell; and
    thereafter photometrically analyzing the liquid in said photometric cell;
    wherein said photometric cell remains in said photometric instrument until after the photometric analysis.

2. The method of claim 1, wherein said photometric cell is rotatably disposed in said photometric instrument and provides more than one optical path length, further comprising selecting an optical path length by rotation of said photometric cell.

3. The method of claim 1, wherein said at least one analytical agent reacts with an analyte in said aqueous sample to produce a photometrically analyzable liquid.

4. The method of claim 1, further comprising prior to the analytical agent delivery step, reacting an analyte in said aqueous sample to yield a reaction product.

5. The method of claim 4, wherein said at least one analytical agent reacts with said reaction product to produce a photometrically analyzable liquid.

6. The method of claim 1, further comprising prior to the analytical agent delivery step, adding an analytical agent reactive with an analyte in said aqueous sample to yield a photometrically analyzable liquid.

7. The method of claim 1, wherein said analytical agent is delivered from a fibrous matrix disposed on said support by wetting-contact of said fibrous matrix with said aqueous sample.

8. The method of claim 7, wherein said fibrous matrix comprises a suitable water soluble barrier.

9. The method of claim 1, wherein said analytical agent is delivered by dissolution of a suitable water soluble carrier disposed on said support.

10. The method of claim 1, wherein the photometric analyzing step is selected from colorimetric and turbidimetric analysis.

11. A photometric analytical method comprising
    adding to a photometric cell disposed in a photometric instrument an aqueous sample to be analyzed;
    obtaining a blank reading;
    then moving a portion of a support of a reagent delivery device in said aqueous sample within said photometric cell, to deliver from the reagent delivery device support into said aqueous sample an effective amount of at least one water soluble analytical agent for photometric analysis, and also to provide a mixing action;

thereafter withdrawing said reagent delivery device from the resulting liquid in said photometric cell; and thereafter photometrically analyzing the liquid in said photometric cell;

wherein said photometric cell remains in said photometric instrument at least until after the photometric analysis.

12. The method of claim 11, wherein said photometric cell is rotatably disposed in said photometric instrument and provides more than one optical path length, further comprising prior to the analytical agent delivery step, selecting an optical path length by rotation of said photometric cell.

13. A photometric analytical method comprising adding an aqueous sample to a photometric cell disposed in a photometric instrument, by introducing at least a portion of said photometric cell into an aqueous liquid to be analyzed;

obtaining a blank reading;

then moving a portion of a support of a reagent delivery device in said aqueous sample, to deliver from the reagent delivery device support into said aqueous sample an effective amount of at least one water soluble analytical agent for photometric analysis;

thereafter withdrawing said reagent delivery device from the resulting liquid in said photometric cell; and thereafter photometrically analyzing the liquid in said photometric cell;

wherein said photometric cell remains in said photometric instrument at least until after the photometric analysis.

14. The method of claim 13, wherein said photometric cell is disposed in a cell chamber located near an end of said photometric instrument and said photometric instrument is a waterproof photometric instrument.

15. The method of claim 13, wherein said photometric cell is sealed in a cell chamber of said photometric instrument.

16. The method of claim 13, wherein said photometric cell is suitably dimensioned comprising having a suitable height, for capturing a desired sample volume.

17. The method of claim 13, wherein said moving said portion of the reagent delivery device support in said aqueous sample, also provides a mixing action.

18. A photometric analytical method comprising adding to a cell chamber of a photometric instrument an aqueous sample to be analyzed;

obtaining a blank reading;

then moving a portion of a support of a reagent delivery device in said aqueous sample within the photometric instrument cell chamber, to deliver from the reagent delivery device support into said aqueous sample an effective amount of at least one water soluble analytical agent for photometric analysis, and also to provide a mixing action;

thereafter withdrawing said reagent delivery device from the resulting liquid in said photometric instrument cell chamber; and thereafter photometrically analyzing the liquid in said photometric instrument cell chamber.

19. A photometric analytical method comprising adding an aqueous sample to a photometric instrument cell chamber, by introducing at least a portion of said cell chamber into an aqueous liquid to be analyzed;

obtaining a blank reading;

then moving a portion of a support of a reagent delivery device in said aqueous sample, to deliver from the reagent delivery device support into said aqueous sample an effective amount of at least one water soluble analytical agent for photometric analysis;

thereafter withdrawing said reagent delivery device from the resulting liquid in said photometric instrument cell chamber; and thereafter photometrically analyzing the liquid in said photometric instrument cell chamber.

20. The method of claim 19, wherein said cell chamber is disposed near an end of said photometric instrument and said photometric instrument is a waterproof photometric instrument.

21. The method of claim 19, wherein said moving said portion of the reagent delivery device support in said aqueous sample, also provides a mixing action.

22. A photometric analytical method comprising disposing a photometric cell that provides more than one optical path length, in a photometric instrument, and selecting an optical path length by rotation of said photometric cell wherein said rotation is limited by contact of a flange of said photometric cell with a stop member;

adding an effective amount of at least one analytical agent for photometric analysis, to a liquid sample in said photometric cell; and thereafter photometrically analyzing the liquid in said photometric cell.

23. A photometric apparatus comprising a photometric instrument provided with a cell chamber for receiving a photometric cell for analysis, wherein said cell chamber is partially surrounded by a raised rim, and a photometric cell that provides more than one optical path length, and comprises a flange, wherein said photometric cell is rotatably disposed in said photometric instrument cell chamber, and the rotation of the photometric cell is limited by contact of said flange with an end of said raised rim, and an optical path length of said photometric cell is thereby positioned relative to a light path of the photometric instrument.

* * * * *